United States Patent [19]

Green

[11] Patent Number: 4,605,769
[45] Date of Patent: Aug. 12, 1986

[54] PREPARATION OF ALKANOLAMINE

[75] Inventor: Michael J. Green, Hedon, England

[73] Assignee: BP Chemicals Limited, London, England

[21] Appl. No.: 743,753

[22] Filed: Jun. 12, 1985

[30] Foreign Application Priority Data

Jun. 21, 1984 [GB] United Kingdom ............... 8415806

[51] Int. Cl.$^4$ ...................... C07C 89/02; C07C 85/02
[52] U.S. Cl. ................................. 564/477; 564/445; 564/476
[58] Field of Search ................. 564/476, 477, 445

[56] References Cited

U.S. PATENT DOCUMENTS 2,786,869  3/1957  de Benneville et al. ............ 564/477
2,871,266  1/1959  Riley ................................... 564/477

Primary Examiner—Charles F. Warren
Assistant Examiner—R. A. Picard
Attorney, Agent, or Firm—Brooks Haidt Haffner & Delahunty

[57] ABSTRACT

Alkanoamines such as diethylaminopropanol is prepared by reacting an alkylene oxide and either an amine or ammonia is the presence of a salt of a fluorosulphonic acid.

12 Claims, No Drawings

PREPARATION OF ALKANOLAMINE

The present invention relates to the preparation of alkanolamines, more particularly to the catalytic preparation of alkanolamines from an alkylene oxide and an amine or ammonia.

Alkanolamines are valuable chemicals, finding application, in the production of soaps and detergents as well as in the cosmetic and agricultural products industries. It is also possible to use alkanolamines in gas purification processes.

Alkanolamines, for example ethanolamine, have previously been prepared by reaction of an alkylene oxide and either an amine or ammonia at elevated temperature. It has now been discovered that improved rates of reaction can be obtained if the reaction is carried out in the presence of, as catalyst, a salt of a fluorosulphonic acid for example triflic acid which is also known as trifluoromethanesulphonic acid.

Accordingly, the present invention provides a process for preparing an alkanolamine from (i) an alkylene oxide and (ii) either ammonia or an amine which process comprises reacting the alkylene oxide and either ammonia or the amine in the presence of an effective amount of a catalyst, characterised in that the catalyst is a salt of a fluorosulphonic acid.

The catalyst may be any salt of a fluorosulphonic acid including but not limited to alkali metal, alkaline earth metal, transition metal, lanthanide, Group III A metal and tetraalkylammonium salts of a fluorosulphonic acid. It is preferable to use Group III A metal fluorosulphonates and more preferred to use aluminium fluorosulphonate as the catalyst for this reaction. The most preferred catalyst is aluminium triflate. The salts described herein have the advantages of being thermally and air stable as well as being relatively easy to prepare. In most cases the fluorosulphonic salt may be prepared by the reaction of a fluorosulphonic acid on the appropriate metal, metal oxide, metal hydroxide or metal carbonate. The fluorosulphonic acid can be any sulphonic acid wherein at least one fluorine atom is present. Preferably, the fluorosulphonic acid is a compound of the general formula $RSO_3H$ wherein R is an alkyl, substituted alkyl or aryl group containing at least one fluorine atom adjacent to the sulphonic acid group. Examples of such R groups include but are not limited to perfluoroethyl, trifluoromethyl, 1,1,2,2-tetrafluoroethyl and the like. Most preferred are alkyl groups which are perfluorinated.

The alkylene oxide used as a reactant can be any alkylene oxide but is conveniently a lower alkylene oxide having less than 20 carbon atoms. Both unsubstituted alkylene oxides, for example ethylene oxide, and substituted alkylene oxides, for example epichlorohydrin may be used. Preferred alkylene oxides are ethylene oxide, propylene oxide, butylene oxide, cyclohexene oxide and epichlorohydrin.

In addition to an alkylene oxide, ammonia or an amine is used as a coreactant. If an amine is used it must have at least one hydrogen connected to the nitrogen atom and hence, primary or secondary amines can be used but not tertiary amines. Preferred amines are lower aliphatic primary and secondary amines having up to 20 carbon atoms in each hydrocarbyl group attached to the nitrogen. The hydrocarbyl group can be substituted or unsubstituted. Examples of preferred amines include but are not limited to dialkylamines e.g. dimethylamine, diethylamine, dipropylamine, methylethylamine and the like and monoalkylamines e.g. ethylamine, propylamine, methylamine and the like.

The molar ratio of reactants will to some extent depend on the nature of the amines used or whether ammonia is used. In general, the molar ratio of amine or ammonia to alkylene oxide should be in the range from 10:1 to 1:10, preferably 10:1 to 1:3. The catalyst is conveniently added in amounts such that it constitutes between 1 and 10,000 ppm by weight of the reactants.

The alkanolamine produced can be, depending on whether ammonia or a primary amine or a secondary amine is used, a monoalkanolamine, a dialkanolamine or a trialkanolamine.

It is possible to carry out the above process at room temperature although higher temperatures can be used to accelerate the rate of reaction. The reaction is preferably carried out at a temperature in the range of 20° to 140° C.

The reaction can be carried out at atmospheric pressure or at a superatmospheric pressure in the range 1 to 20 bar. Preferably the reaction is carried out under the autogenous pressure generated by the reaction mixture in a closed vessel at the temperature of reaction.

The reaction can be carried out batchwise or continuously.

The following examples illustrate the present invention. However, the scope of the present invention shall not be limited by the examples, the invention including equivalent modifications, variations and embodiments.

EXAMPLE 1

A 100 ml round bottom flask was charged with 20 g of diethylamine, 6.7 g of propylene oxide and 0.0037 g of the aluminium salt of trifluoromethanesulphonic acid (aluminium triflate) and the resulting mixture stirred at room temperature. Aliquots of the liquid product removed after 24 hours and 72 hours stirring showed, by gas chromatography, a propylene oxide conversion to diethylaminopropanol of 14 and 52% respectively.

COMPARATIVE EXAMPLE A

Example 1 was repeated in the absence of aluminium triflate. Analysis of the liquid product after 24 and 72 hours showed a propylene oxide conversion to diethylaminopropanol of 0 and 1% respectively.

EXAMPLE 2

A Fischer-Porter tube was charged with 20 g of diethylamine, 6.7 g of propylene oxide and 0.027 g of aluminium triflate. The tube was sealed and purged with nitrogen to remove air, pressurised to 50 psi with nitrogen, sealed, and finally heated to 80° C. with stirring. After 2 hours the tube was cooled and depressurised. Analysis of the liquid product by gas chromatography showed a 34% conversion of propylene oxide to diethylaminopropanol.

COMPARATIVE EXAMPLE B

Example 2 was repeated in the absence of aluminium triflate. Analysis of the liquid product showed a propylene oxide conversion of less than 1% to diethylaminopropanol.

EXAMPLE 3

Example 2 was repeated at 100° C. Analysis of the liquid product showed a propylene oxide conversion of 55% to diethylaminopropanol.

EXAMPLE 4

Example 2 was repeated at 120° C. Analysis of the liquid product showed a propylene oxide conversion of 68% to diethylaminopropanol.

EXAMPLE 5

Example 4 was repeated but in the presence of 0.0027 g of aluminium triflate. Analysis of the liquid product showed a propylene oxide conversion of 25% to diethylaminopropanol.

EXAMPLE 6

Example 3 was repeated except that 6.7 g of 1,2-butylene oxide was used in place of propylene oxide. Analysis of the liquid product showed a butylene oxide conversion of 65% to diethylaminobutanol.

EXAMPLE 7

Example 3 was repeated but using 20 g of n-butylamine in place of diethylamine. Analysis of the liquid product showed a quantitative conversion of propylene oxide to butylaminopropanol.

I claim:

1. A process for the preparation of an alkanolamine comprising reacting an alkylene oxide with either an amine or ammonia in the presence of an effective amount of a catalyst comprising a salt of a fluorosulphonic acid, said fluorosulphonic acid being a compound of the formula $RSO_3H$ where R is an alkyl, substituted alkyl, or aryl group, containing at least one fluorine atom adjacent to the sulphonic acid group, and said amine having at least one hydrogen connected to the nitrogen atom.

2. The process of claim 1 wherein the salt of a fluorosulphonic acid constitutes between 1 and 10,000 ppm.

3. The process of claim 2 wherein the molar ratio of amine or ammonia to alkylene oxide is in the range from 10:1 to 1:10.

4. The process of claim 3 wherein the salt of a fluorosulphonic acid is a Group III A metal fluorosulphonate.

5. The process of claim 4 wherein the salt of a fluorosulphonic acid is aluminium triflate.

6. The process of claim 3 wherein the alkylene oxide is selected from ethylene oxide, propylene oxide, butylene oxide, cyclohexene oxide and epichlorohydrin.

7. The process of claim 3 wherein the amine is a monoalkylamine or a dialkylamine.

8. The process of claim 1 wherein the process is conducted at a temperature of 20° to 140° C.

9. The process of claim 1, wherein R is selected from the group consisting of perfluoroethyl, trifluoromethyl, and 1,1,2,2-tetrafluoroethyl.

10. The process of claim 9, wherein R is trifluoromethyl.

11. The process of claim 1, wherein said amine is selected from the group consisting of dimethylamine, diethylamine, dipropylamine, methylethylamine, ethylamine, propylamine, methylamine and n-butylamine.

12. The process of claim 1, wherein said salt of said fluorosulphonic acid is selected from the group consisting of an alkali metal salt, an alkaline earth metal salt, a transition metal salt, a lanthanide salt, a Group III A metal salt, and a tetraalkylammonium salt of said fluorosulphonic acid.

* * * * *